United States Patent [19]

Omura

[11] Patent Number: 4,757,711

[45] Date of Patent: Jul. 19, 1988

[54] OSCILLOSCOPIC HAND-DYNAMOGRAPHIC TRANSDUCER

[76] Inventor: Yoshiaki Omura, Apt. 8-I, Riverside Dr., New York, N.Y. 10023

[21] Appl. No.: 890,808

[22] Filed: Jul. 24, 1986

Related U.S. Application Data

[63] Continuation of Ser. No. 692,855, Jan. 16, 1985, abandoned, which is a continuation of Ser. No. 614,397, May 25, 1984, abandoned, which is a continuation of Ser. No. 429,342, Sep. 30, 1982, abandoned.

[51] Int. Cl.⁴ .......................... A61B 5/22; H01C 10/10
[52] U.S. Cl. ..................................... 73/379; 73/862.58; 338/47
[58] Field of Search ............ 73/379, 380, 381, 862.58; 272/68, DIG. 5; 340/688; 338/13, 47, 198

[56] References Cited

U.S. PATENT DOCUMENTS

| | | | |
|---|---|---|---|
| 468,154 | 2/1892 | McClure | 73/381 |
| 2,894,179 | 7/1959 | Knudsen | 340/688 X |
| 3,216,259 | 11/1965 | Bendix | 73/380 |
| 3,281,684 | 10/1966 | Reeds | 340/688 X |
| 3,466,931 | 9/1969 | Spackman, Jr. et al. | 73/380 |
| 3,672,219 | 6/1972 | Van Patten | 73/379 |
| 3,680,386 | 8/1972 | Cannon | 73/379 X |
| 4,322,711 | 3/1982 | Spangler et al. | 338/198 X |

OTHER PUBLICATIONS

"Normal and Abnormal Relationship Between Brain Circulation...", Acupuncture & Electro-Ther A Peut. Res., in J vol. 3, pp. 49-96, 1978 by Yoshiaki Omura, M.D., SC.D., F.A.C.A.

Primary Examiner—Joseph A. Orsino
Assistant Examiner—Brian R. Tumm
Attorney, Agent, or Firm—Richard B. Klar

[57] ABSTRACT

A dynamometer comprising a first member, a second member which is movable relative to the first member along a predetermined path, a piston and cylinder arrangement for resisting movement of the second member with respect to the first member in one direction along the predetermined path with a force which increases from zero with the distance moved from a rest position, and a potentiometer having a first elongate resistor element having two ends and a second wiper element which is in electrical contact with the resistor element and is movable with respect thereto to establish an electrical resistance between the wiper element and one end of the resistor element which increases with relative movement of the elements in one direction. One of the elements of the potentiometer is fixedly mounted on the first member, and the other element is coupled to the second member so that movement of the second member along the predetermined path away from the rest position is accompanied by relative movement of the elements in the direction to increase the electrical resistance between the wiper element and the end of the resistor element.

11 Claims, 2 Drawing Sheets

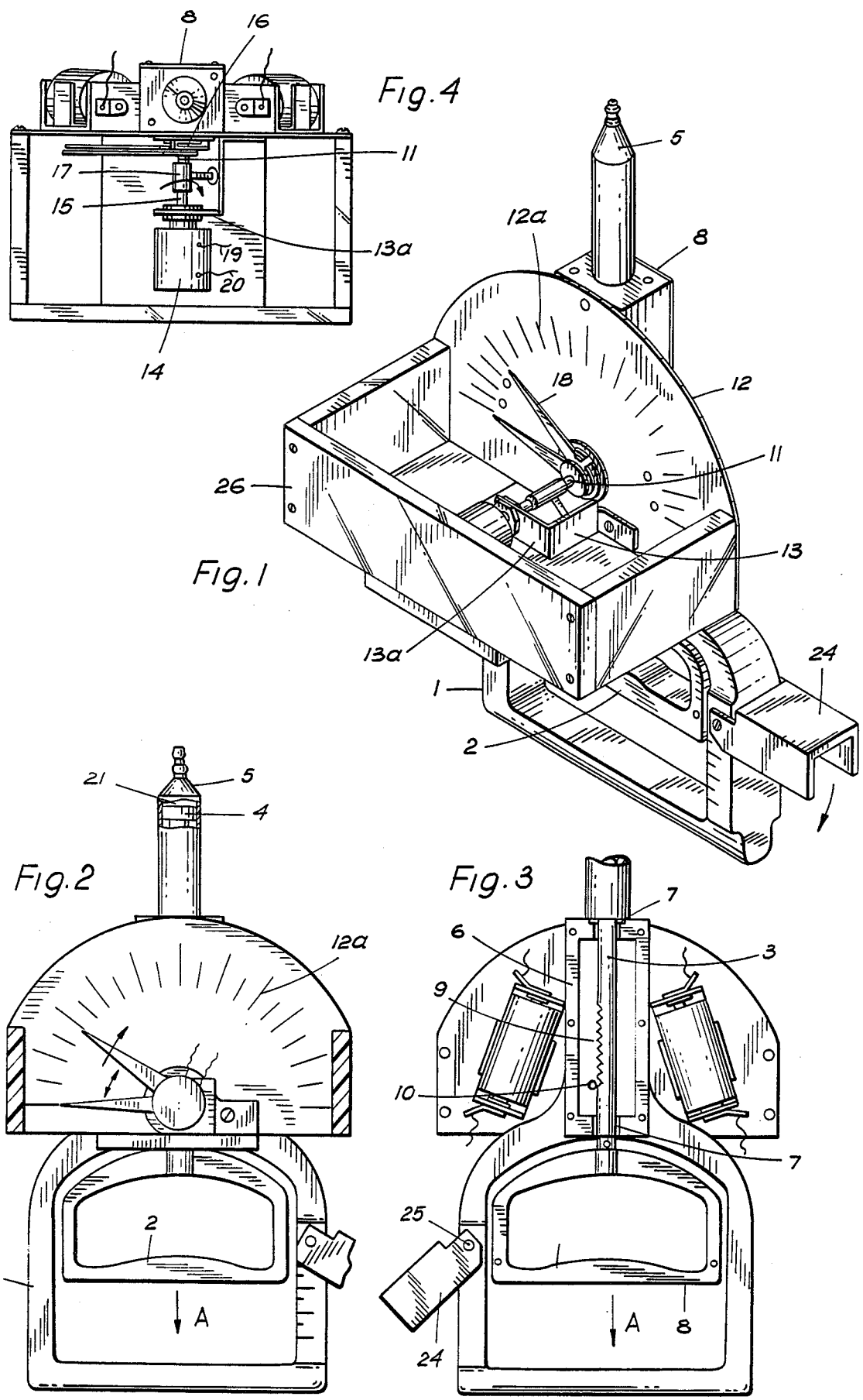

OSCILLOSCOPIC HAND-DYNAMOGRAPHIC TRANSDUCER

This is a continuation of co-pending application Ser. No. 692,855, filed on Jan. 16, 1985, now abandoned, which is a continuation of application Ser. No. 614,397, filed May 25, 1984, now abandoned, which is a continuation of application Ser. No. 429,342, filed 9/30/82, now abandoned.

SUMMARY OF THE INVENTION

This invention relates to dynamometers.

According to one aspect of the present invention there is provided a dynamometer, comprising a first member, a second member which is movable relative to the first member along a predetermined path, means for resisting movement of the second member with respect to said first member in one direction along said predetermined path with a force which increases with the distance moved in said one direction, and a multiturn rotary potentiometer having a first resistor element and a second wiper element which is in sliding electrical contact with the resistor element and is rotatable with respect thereto to establish an electrical resistance between the wiper element and one end of the resistor element which increases with relative rotation of said elements in one sense, one of said first and second elements being fixedly mounted on said first member, and the dynamometer further comprising means coupling the other of said first and second elements to said second member so that movement of said second member in said one direction along said predetermined path is accompanied by relative rotation of said elements in said one sense.

According to another aspect of the present invention there is provided a dynamometer, comprising a first member, a second member which is movable with respect to the first member along a predetermined path, means for resisting movement of the second member with respect to said first member in one direction along said predetermined path with a force which increases from zero with the distance moved in said one direction from a rest position of the second member, a potentiometer having a first elongate resistor element having two ends and a second wiper element which is in sliding electrical contact with the resistor element and is movable with respect thereto to establish an electrical resistance between the wiper element and one end of the resistor element which increases with relative movement of said elements in one direction, one of said first and second elements being fixedly mounted on said first member, the dynamometer also comprising means coupling the other of said first and second elements to said second member so that movement of said second member in said one direction along said predetermined path is accompanied by relative movement of said elements in the direction to increase said electrical resistance, said wiper element being spaced from said one end of the resistor element when the second member is in its rest position, and the dynamometer further comprising means to develop a potential difference between said wiper element and said one end of the resistor element which is dependent upon the electrical resistance therebetween, and means to develop an opposing potential difference substantially equal to the potential difference between said wiper element and said one end of the resistor element when said second member is in its rest position, whereby the resulting potential difference is brought to substantially zero.

BRIEF DESCRIPTION OF THE DRAWINGS

For a better understanding of the invention, and to show how the same may be carried into effect, reference will now be made, by way of example, to the accompanying drawings in which:

FIG. 1 shows a perspective view of a dynamometer;
FIG. 2 shows a front elevation of the dynamometer;
FIG. 3 shows a rear elevation of the dynamometer with a part removed;
FIG. 4 shows a plan view of the dynamometer.

DESCRIPTION OF THE PREFERRED EMBODIMENT

Figure 5:
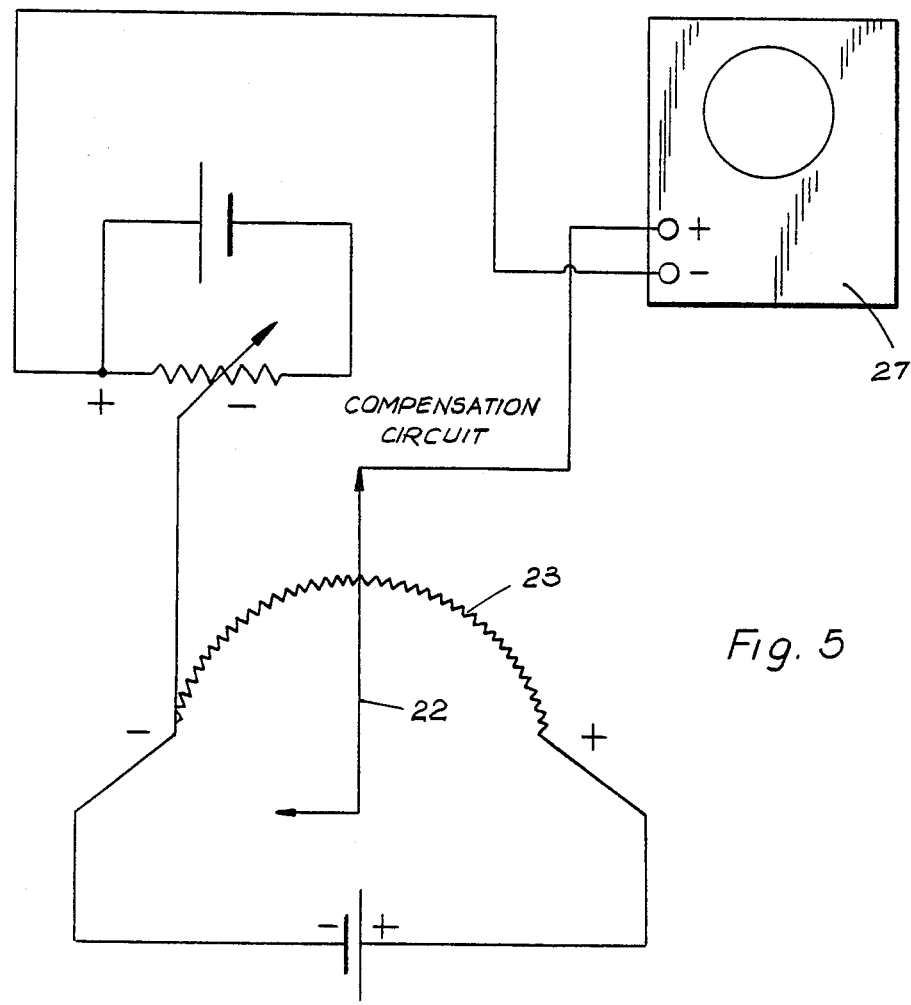
FIG. 5 shows a circuit diagram.

The illustrated dynamometer comprises a frame 1 defining an opening in which a handle 2 is received. The handle 2 is attached to a shaft 3 which carries a piston 4. The piston 4 is received in a cylinder 5. The space 21 in the cylinder above the piston 4 is sealed. Between the cylinder 5 and the frame 1 is a housing 6, through which the shaft 3 extends. The housing 6 is formed with guide apertures 7 which define a path of movement for the shaft 3 and thus for the handle 2, relative to the frame 1. Accordingly, the handle 2 is able to move relative to the frame 1 only in directions parallel to the axis of the shaft 3. The housing is shown as being open in FIG. 3, but it would normally be closed by a rear cover plate 8 as shown in FIGS. 1 and 4.

The housing 6 is closed at the front by a generally semicircular dial 12 which is provided with graduations 12a. Secured to the dial at its bounding diameter is a bracket 13. The bracket 13 includes a part 13a extending parallel to, but spaced from, the dial 12, and the part 13a carries a multiturn potentiometer 14. The potentiometer has a rotary shaft 15 which extends towards the center of curvature of the semicircular dial 12. The potentiometer has a first terminal 19 connected to the wiper 22 (FIG. 5) of the potentiometer and a second terminal 20 connected to one end of the resistor 23.

As can be seen in FIG. 3, the shaft 3 is provided at one side with teeth forming a rack 9, and this rack engages a pinion 10 which is mounted on a shaft 11. The shaft 11 is coaxial with the shaft 15 of the potentiometer 14, and is mounted in a bushing 16 secured to the dial 12. The shaft 11 extends through the dial 12 and is connected to the shaft 15 by a sleeve 17. Between the dial 12 and the sleeve 17, the shaft 11 carries a needle 18. The point of the needle passes over the scale 12 in proximity to the graduations 12a. The scale 12 is graduated in kilograms force required to move the handle 2 relative to the frame 1 against the resistance of the piston 4 in the cylinder 5.

In order to limit rotation of the handle 2 relative to the frame 1 about the axis of the shaft 3, a U-shaped guide member 24 is hinged to the frame 1 at 25 and can be disposed in a first position in which it prevents such rotation or in a second position (illustrated in FIGS. 1, 2 and 3) in which it permits such rotation.

When the handle 2 is moved relative to the frame 1, in the direction of the arrow A, a measure of the force applied to the handle is provided not only by the needle 18 but also by the electrical resistance between the two terminals 19 and 20 of the potentiometer.

In order to protect the potentiometer 14 and its mounting bracket 13, a transparent guard 26 is secured to the dial 12.

One problem with multiturn potentiometers is that when the wiper is at one end of the resistor, electrical noise is generated when the wiper moves over the resistor away from the end. The amplitude of noise produced during movement of the wiper is much less when the wiper is well away from the ends of the resistor. Accordingly, in the present invention the potentiometer shaft 15 is secured to the shaft 11 by the sleeve 17 in such manner that when the handle is in its rest position, in which no force is applied to the handle 2 to move it relative to the frame 1 in the direction of the arrow A, the wiper 22 of the potentiometer is spaced from the ends of the resistor 23. When force is applied to the handle 2 to move it in the direction of the arrow A, the wiper moves over the resistor without generating the amplitude of noise that arises when the wiper moves over the resistor at the end of the resistor. Of course, this arrangement results in the electrical resistance between the terminals 19 and 20 being non-zero when the force applied to the handle is zero. The circuit illustrated in FIG. 5 compensates for this residual resistance.

The output of the compensation circuit is connected to the Y input of an oscilloscope 27 which may be provided with a camera. If a patient is then instructed to grip the potentiometer, by placing the base of the frame 1 across the palm of his hand and extending his fingers about the handle 2, and thereby pull the handle 2 towards the base of the frame 1 in the direction of the arrow A, the manner in which the force applied to the handle 2 varies in time is shown by the trace on the oscilloscope screen and may be recorded by use of the camera. It has been found that the smoothness of the increase in force, and the duration for which the maximum force can be maintained, are useful diagnostic tools.

I claim:

1. A dynamometer, comprising a first member, a second member which is mechanically movable relative to the first member along a predetermined path, means for resisting movement of the second member with respect to said first member in one direction along said predetermined path with a force which increases with the distance moved in said one direction, and a multiturn rotary potentiometer to provide resolution and having an axis, a resistor element and a wiper element which is in sliding electrical contact with the resistor element and is rotatable with respect thereto establishing an electrical resistance between the wiper element and one end of the resistor element which increases with relative rotation of said elements in one sense, one of said resistor and wiper elements being fixedly mounted on said first member, and the dynamometer further comprising means coupling the other of said resistor and wiper elements to said second member to provide direct electrical measurement of the mechanical movement of said second member by means of said electrical resistance so that movement of said second member in said one direction along said predetermined path is accompanied by relative rotation of said elements in said one sense, said coupling means including a shaft having an axis and being rotatable thereabout, the axis of said shaft being coaxially aligned with the axis of said potentiometer, one end of said shaft being pivotally connected to said potentiometer and another end of said shaft being pivotally interconnected to said second member and an L-shaped bracket connected to said potentiometer wherein said shaft and said bracket ensure an accurate measurement of the movement of said second member.

2. A dynamometer as claimed in claim 1, wherein said first member comprises a frame member and said second member comprises a handle member which is movable in directions towards and away from the frame member, and said means for resisting movement of the handle member with respect to the frame member resist movement of the handle member towards the frame member, whereby said electrical resistance provides a measure of the force moving the handle member towards the frame member.

3. A dynamometer as claimed in claim 1, wherein said other of said resistor and wiper elements of the potentiometer comprises the wiper element, and the means coupling the wiper element to said second member comprise said rotary shaft connected to the wiper element, a pinion carried by the rotary shaft, and a toothed member connected to said second member and in engagement with said pinion.

4. A dynamometer as claimed in claim 3, wherein said predetermined path is rectilinear, and said toothed member comprises a rack which is connected to said second member and which extends parallel to said predetermined path.

5. A dynamometer as claimed in claim 1, further comprising a dial provided with a graduated scale and a pointer member mounted to move over said scale, said second member being connected to said pointer member whereby movement of said second member in said one direction along said predetermined path is accompanied by movement of the pointer member over said graduated scale.

6. A dynamometer as claimed in claim 1 where said potentiometer has an offset voltage applied thereto so as to avoid noises which would interfere with an accurate electrical measurement of the mechanical movement of said second member.

7. A dynamometer, comprising a first member, a second member which is mechanically movable with respect to the first member along a predetermined path, means for resisting movement of the second member with respect to said first member in one direction along said predetermined path with a force which increases from zero with the distance moved in said one direction from a rest position of the second member, a linear potentiometer having a first elongate resistor element having two ends and an internal wiper element which is in sliding electrical contact with the resistor element and is movable with respect thereto to establish an electrical resistance between said wiper element and one end of the resistor element which increases with relative movement of said elements in one direction, one of said resistor and wiper elements being fixedly mounted on said first member, the dynamometer also comprising means coupling the other of said resistor and wiper elements to said second member to provide direct electrical measurement of the mechanical movement of said second member by means of said electrical resistance so that movement of said second member in said one direction along said predetermined path is accompanied by relative movement of said elements in the direction to increase said electrical resistance, said wiper element being spaced from said one end of the resistor element when the second member is in its rest position, and the dynamometer further comprising means to develop a potential difference between said wiper element and said one end of the resistor therebetween, and means to develop an opposing potential difference substantially equal to the potential difference between said wiper element and said one end of the resistor element when said second member is in its rest position whereby the resulting potential difference is brought to substantially zero, and said coupling means including a shaft having an axis and being rotatable thereabout the axis of said shaft being axially aligned with the axis of said potentiometer, one end of said shaft being, pivotably connected to said potentiometer and another end of said shaft being pivotably interconnected to said second member and an L-shaped bracket connected to said potentiometer wherein said shaft and said bracket ensure an accurate measurement of the movement of said second member.

8. A dynamometer as claimed in claim 7, wherein said potentiometer is a multiturn rotary potentiometer and the other of said resistor and wiper elements of the potentiometer comprises the wiper element, and the means coupling the wiper element to said second member comprise said rotary shaft connected to the wiper element, a pinion carried by the rotary shaft, and a toothed member connected to said second member and in engagement with said pinion.

9. A dynamometer as claimed in claim 8, wherein said predetermined path is rectilinear, and said toothed member comprises a rack which is connected to said second member and which extends parallel to said predetermined path.

10. A dynamometer as claimed in claim 9, further comprising a dial provided with a graduated scale and a pointer member mounted to move over said scale, said second member being connected to said pointer member whereby movement of said second member in said one direction along said predetermined path is accompanied by movement of the pointer member over said graduated scale.

11. A dynamometer as claimed in claim 7, wherein said first member comprises a frame member and said second member comprises a handle member which is movable in directions towards and away from the frame member, and said means for resisting movement of the handle member with respect to the frame member resist movement of the handle member towards the frame member, whereby said electrical resistance provides a measure of the force moving the handle member towards the frame member.

* * * * *